United States Patent [19]

Pastor et al.

[11] Patent Number: 5,391,799
[45] Date of Patent: Feb. 21, 1995

[54] PROCESS FOR THE PREPARATION 6-CHLORO-2,4,8,10-TETRA-BUTYLDIBENZO[D,F][1,3,2]DIOXAPHOSHEPIN

[75] Inventors: Stephen D. Pastor, Danbury, Conn.; Sai P. Shum, Pleasantville, N.Y.

[73] Assignee: Ciba-Geigy Corporation, Ardsley, N.Y.

[21] Appl. No.: 220,982

[22] Filed: Mar. 1, 1994

Related U.S. Application Data

[63] Continuation-in-part of Ser. No. 983,108, Nov. 30, 1992, Pat. No. 5,292,785, which is a continuation of Ser. No. 878,675, May 5, 1992, abandoned.

[51] Int. Cl.$^6$ .................................. C07F 9/6574
[52] U.S. Cl. ........................... 558/96; 558/73
[58] Field of Search ..................... 558/96, 101

[56] References Cited

U.S. PATENT DOCUMENTS

| | | | |
|---|---|---|---|
| 3,297,631 | 1/1967 | Bown et al. | 524/117 |
| 3,476,649 | 11/1969 | Kauder et al. | 524/117 |
| 3,907,939 | 9/1975 | Robin et al. | 558/90 |
| 4,318,845 | 3/1982 | Spivack et al. | 524/117 |
| 4,381,359 | 4/1983 | Idel et al. | 524/117 |
| 4,835,299 | 5/1989 | Maher et al. | 558/85 |
| 4,912,155 | 3/1990 | Burton | 524/118 |
| 4,999,393 | 3/1991 | Haruna et al. | 524/126 |
| 5,059,710 | 10/1991 | Abatjoglou et al. | 558/78 |
| 5,126,475 | 6/1992 | Bahrmann et al. | 558/85 |

FOREIGN PATENT DOCUMENTS

| | | | |
|---|---|---|---|
| 1543531 | 9/1969 | Germany | 558/101 |
| 2940620 | 4/1981 | Germany | 558/96 |

OTHER PUBLICATIONS

Pastor, et al. Helvetica Chimica Acta–vol. 76, 900–914 (1993).

*Primary Examiner*—Veronica P. Hoke
*Attorney, Agent, or Firm*—Luther A. R. Hall

[57] ABSTRACT

6-Chloro-2,4,8,10-tetrabutyl-dibenzo[d,f][1,3,2]dioxaphosphepin and related phosphorochlorites are prepared by reaction of an appropriate bisphenol with phosphorus trichloride in the presence of a catalytic amount of 1-methyl-2-pyrrolidinone in toluene followed by heating the solution and stripping off the hydrogen chloride formed by a flow of nitrogen.

14 Claims, No Drawings

PROCESS FOR THE PREPARATION 6-CHLORO-2,4,8,10-TETRA-BUTYLDIBENZO[D,F][1,3,2]DIOXAPHOSHEPIN

This is a continuation-in-part of application Ser. No. 07/983,108, filed Nov. 30, 1992, now U.S. Pat. No. 5,292,785, which is a continuation of application Ser. No. 07/878,675, filed May 5, 1992, now abandoned.

BACKGROUND OF THE INVENTION

Organic materials such as polymers, resins, lubricating oils and the like are often subject to thermal, oxidative and actinic induced degration. Various stabilizers including the organic phosphites have been developed to stabilize such materials.

Cyclic phosphites have achieved a firm place among the organic phosphite stabilizers. Typical of such organic phosphites are those taught in U.S. Pat. No. 4,318,845. In order to prepare such organic phosphite stabilizers, a key intermediate is first prepared by reacting an appropriate bisphenol with phosphorus trichloride to prepare the corresponding phosphorochloridite in the presence of an acid acceptor such as triethylamine.

DETAILED DESCRIPTION

The instant invention pertains to a simplified process for preparing such intermediates by reacting the appropriate bisphenol with phosphorus trichloride in an organic solvent such as toluene in the presence of a small catalytic amount of 1-methyl-2-pyrrolidinone, maintaining the solution at room temperature or hearing the solution at temperatures up to 150° C., and passing a slow stream of nitrogen through the solution till the evolution of hydrogen chloride ceases. The phosphorochloridite intermediate is then recovered from the solution in a conventional manner in essentially quantitative yield.

More particularly, the instant invention pertains to a process for the preparation of a compound of formula I

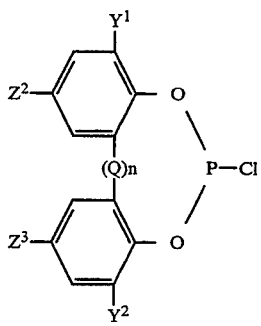

wherein
n has a value of 0 or 1;
when n is 0, Q is a direct bond,
when n is 1, Q is —$CR^1R^2$— wherein each $R^1$ and $R^2$ independently represents hydrogen, straight chain alkyl of 1 to 18 carbon atoms, branched chain alkyl of 1 to 12 carbon atoms, phenyl, tolyl or anisyl;
each $Y^1$, $Y^2$, $Z^2$ and $Z^3$ independently represents hydrogen, a straight or branched chain alkyl of 1 to 18 carbon atoms, bicycloalkyl of 7 to 10 carbon atoms, phenyl, benzyl, 1-phenylethyl, cyclohexyl, 1-methylcyclohexyl, cyano, halogen, nitro, trifluoromethyl, hydroxy, amino, alkanoyl of 2 to 18 carbon atoms, alkoxy of 1 to 18 carbon atoms or $E^1E^2E^3Si$ where $E^1$, $E^2$ and $E^3$ are independently hydrogen, alkyl of 1 to 4 carbon atoms or phenyl;
which process comprises
reacting a bisphenol of formula II

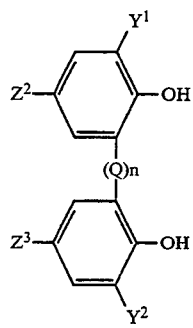

with phosphorus trichloride in an organic solvent containing 1-methyl-2-pyrrolidinone, where the molar ratio of bisphenol to phosphorus trichloride is from 1:1 to 1:10, preferably from 1:1 to 1:3, and the amount of 1-methyl-2-pyrrolidinone catalyst is from 1 to 20 mol percent, preferably from 5 to 10 mol percent, based on the bisphenol,
  maintaining the temperature of the solution from room temperature to about 150° C., preferably from about 60° to about 120° C., most preferably from about 60° to about 100° C., while passing a stream of nitrogen through the solution till the evolution of hydrogen chloride essentially stops, and
  isolating the phosphorochloridite product.

The organic solvent useful in this process is selected from the group consisting of the inert aliphatic, cycloaliphatic or aromatic hydrocarbons, ethers or chlorinated hydrocarbons. Since the reaction is conveniently carried out while the solvent is being refluxed, the boiling point of the solvent essentially determines the temperature at which the reaction is carried out. Thus, the judicious choice of solvent determines the temperature at which the process is run. Although the 1-methyl-2-pyrrolidinone catalyst is effective at room temperature, the reaction occurs much more rapidly at higher temperatures. Suitable solvents for the instant process include inter alia benzene, toluene, xylene, ethylbenzene, cumene, hexane, heptane, octane, nonane, cyclohexane, diethyl ether, tetrahydrofuran, dioxane, ethylene glycol dimethyl ether, ethylene glycol diethyl ether, methylene chloride, 1,1,2-trichloroethane, trichloroethylene and tetrachloroethylene. Preferably, the solvent is cyclohexane, toluene, xylene, hexane, heptane, octane or nonane; most preferably toluene or xylene.

While the phosphorochloridites can be prepared using acid acceptors such as triethylamine, the instant process using 1-methyl-2-pyrrolidinone catalyst results in fewer undesired side products, such as the reaction product of two moles of bisphenol with one mole of phosphorus trichloride which is hard to avoid when an acid acceptor such as triethylamine is used.

EXAMPLE 1

6-Chloro-2,4,8,10-tetra-tert-butyl-dibenzo[d,f][1,3,2]dioxaphosphepin

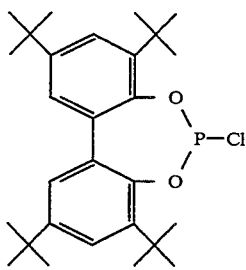

S. D. Pastor et al., Helv. Chim. Acta, 76,900 (1993) describe the preparation of the title compound as seen below. Into a solution of 20 g (49 mmol) of 2,2'-bis(4,6-di-tert-butylphenol) and 0.48 g (4.8 mmol) of 1-methyl-2-pyrrolidinone in 200 mL of toluene is added dropwise 10 g (73 mmol) of phosphorus trichloride at ambient temperature. After addition is complete, the reaction mixture is heated to 95° C. for 17 hours. A slow stream of nitrogen is used to removed hydrogen chloride. The reaction mixture is filtered and the filtrate is concentrated in vacuo to give 23.14 g (99% yield) of a white solid.

$^{31}$P NMR (200 MHz)(Benzene-d$_6$) (ppm): 173.3 ppm

EXAMPLE 2

6-Chloro-2,4,8, 10-tetra-tert-butyl-12-methyl-12 H-dibenzo[d,g][1,3,2]dioxaphosphocin The procedure of Example 1 is repeated using 21.5 g (49 mmol) of 2,2'-ethylidene-bis(2,4-di-tert-butyl-phenol), 0.48 g (4.9 mmol) of 1-methyl-2-pyrrolidinone, 10 g (73 mmol) of phosphorus trichloride and 400 mL of toluene. Trituration of the crude product obtained with 200 mL of acetonitrile gives the 18.9 g (77% yield) of the title compound as a white solid.

EXAMPLES 3–9

Following the general procedure of Example 1, the following compounds are prepared:
  (a) (2,2'-methylene-bis-[4,6-di-tert-butylphenyl]) phosphorochloridite;
  (b) (2,2'-methylene-bis-[4,6-di-tert-amylphenyl]) phosphorochloridite;
  (c) (3,3'-di-tert-butyl-5,5'-dimethyl-1,1'- biphenyl-2,2'-diyl) phosphorochloridite;
  (d) (2,2'-methylene-bis-[4-tert-butyl-6-methylphenyl] phosphorochloridite;
  (e) (2,2'-n-butylidene-bis-[4,6-di-tert-butylphenyl] phosphorochloridite;
  (f) (3,3',5,5'-tetra-octyl-1,1'-biphenyl-2,2'-diyl) phosphorochloridite; and
  (g) (2,2'-methylene-bis-[4,6-ditert-octylphenyl]) phosphorochloridite.

What is claimed is:

1. A process for the preparation of a compound of formula I

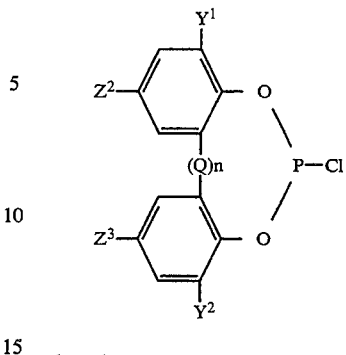

wherein
n has a value of 0 or 1;
when n is 0, Q is a direct bond,
when n is 1, Q is —CR$^1$R$^2$ wherein each R$^1$ and R$^2$ independently represents hydrogen, straight chain alkyl of 1 to 18 carbon atoms, branched chain alkyl of 1 to 12 carbon atoms, phenyl, tolyl or anisyl;
each Y$^1$, Y$^2$, Z$^2$ and Z$^3$ independently represents hydrogen, a straight or branched chain alkyl of 1 to 18 carbon atoms, bicycloalkyl of 7 to 10 carbon atoms, phenyl, benzyl, 1-phenylethyl, cyclohexyl, 1-methylcyclohexyl, cyano, halogen, nitro, trifluoromethyl, hydroxy, amino, alkanoyl of 2 to 18 carbon atoms, alkoxy of 1 to 18 carbon atoms or E$^1$E$^2$E$^3$Si where E$^1$, E$^2$ and E$^3$ are independently hydrogen, alkyl of 1 to 4 carbon atoms or phenyl;
which process comprises
reacting a bisphenol of formula II

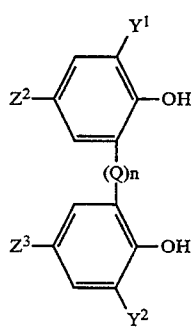

with phosphorus trichloride in an organic solvent containing 1-methyl-2-pyrrolidinone, where the molar ratio of bisphenol to phosphorus trichloride is from 1:1 to 1:10, and the amount of 1-methyl-2-pyrrolidinone catalyst is from 1 to 20 mol percent, based on the bisphenol,
  maintaining the temperature of the solution from room temperature to about 150° C., while passing a stream of nitrogen through the solution till the evolution of hydrogen chloride essentially stops, and
  isolating the phosphorochloridite product.

2. A process according to claim 1 where in the compound of formula I, Y$^1$ and Y$^2$ are tert-butyl, tert-amyl or tert-octyl, Z$^2$ and Z$^3$ are methyl, tert-butyl, tert-amyl or tert-octyl, n is 0 or 1, and Q is a direct bond when n is 0, and Q is methylene, ethylidene or 2,2-butylidene when n is 1.

3. A process according to claim 2 where in the compound of formula I, n is 0, Q is a direct bond and Y$^1$, Y$^2$, Z$^2$ and Z$^3$ are each tert-butyl.

4. A process according to claim 1 wherein the compound of formula I is 6-chloro-2,4,8,10-tetra-tert-butyl-dibenzo[d,f][1,3,2]dioxaphosphepin.

5. A process according to claim 1 wherein the compound of formula I is 6-chloro-2,4,8,10-tetra-tert-butyl-dibenzo[d,g][1,3,2]dioxaphosphocin.

6. A process according to claim 1 wherein the compound of formula I is
(a) (2,2'-methylene-bis-[4,6-di-tert-butylphenyl]) phosphorochloridite;
(b) (2,2'-methylene-bis-[4,6-di-tert-amylphenyl]) phosphorochloridite;
(c) (3,3'-di-tert-butyl-5,5'-dimethyl-1,1'-biphenyl-2,2'-diyl) phosphorochloridite;
(d) (2,2'-methylene-bis-[4-tert-butyl-6-methylphenyl] phosphorochloridite;
(e) (2,2'-n-butylidene-bis-[4,6-di-tert-butylphenyl] phosphorochloridite;
(f) (3,3',5,5'-tetra-octyl-1,1'-biphenyl-2,2'-diyl) phosphorochloridite; or
(g) (2,2'-methylene-bis-[4,6-ditert-octylphenyl]) phosphorochloridite.

7. A process according to claim 1 where the molar ratio of bisphenol to phosphorus trichloride is from 1:1 to 1:3.

8. A process according to claim 1 where the amount of 1-methyl-2-pyrrolidinone catalyst is from 5 to 10 mol percent, based on the bisphenol.

9. A process according to claim 1 where the temperature of the solution is from about 60° to about 120° C.

10. A process according to claim 1 where the temperature of the solution is from about 60° to about 100° C.

11. A process according to claim 1 wherein the organic solvent is selected from the group consisting of the inert aliphatic, cycloaliphatic or aromatic hydrocarbons, ethers or chlorinated hydrocarbons.

12. A process according to claim 11 wherein the organic solvent is benzene, toluene, xylene, ethylbenzene, cumene, hexane, heptane, octane, nonane, cyclohexane, diethyl ether, tetrahydrofuran, dioxane, ethylene glycol dimethyl ether, ethylene glycol diethyl ether, methylene chloride, 1,1,2-trichloroethane, trichloroethylene and tetrachloroethylene.

13. A process according to claim 12 wherein the organic solvent is cyclohexane, toluene, xylene, hexane, heptane, octane or nonane.

14. A process according to claim 13 wherein the organic solvent is toluene or xylene.

* * * * *